(12) United States Patent
Krause

(10) Patent No.: US 10,799,636 B2
(45) Date of Patent: Oct. 13, 2020

(54) FILLING NEEDLE FOR DISPENSING A PHARMACEUTICAL LIQUID INTO A CONTAINER, AND FILLING DEVICE

(71) Applicant: Syntegon Technology GmbH, Waiblingen (DE)

(72) Inventor: Bjoern Krause, Crailsheim (DE)

(73) Assignee: SYNTEGON TECHNOLOGY GMBH, Waiblingen (DE)

( * ) Notice: Subject to any disclaimer, the term of this patent is extended or adjusted under 35 U.S.C. 154(b) by 0 days.

(21) Appl. No.: 16/762,523

(22) PCT Filed: Sep. 5, 2018

(86) PCT No.: PCT/EP2018/073851
§ 371 (c)(1),
(2) Date: May 8, 2020

(87) PCT Pub. No.: WO2019/091622
PCT Pub. Date: May 16, 2019

(65) Prior Publication Data
US 2020/0268972 A1    Aug. 27, 2020

(30) Foreign Application Priority Data
Nov. 8, 2017 (DE) .......... 10 2017 219 811

(51) Int. Cl.
*A61M 5/24* (2006.01)
*B65B 39/00* (2006.01)
(Continued)

(52) U.S. Cl.
CPC ............ *A61M 5/24* (2013.01); *A61M 5/3202* (2013.01); *B65B 3/003* (2013.01); *B65B 39/001* (2013.01); *A61M 2005/3114* (2013.01)

(58) Field of Classification Search
CPC ................. A61M 5/24; A61M 5/3202; A61M 2005/3114; B65B 3/003; B65B 39/001
See application file for complete search history.

(56) References Cited

U.S. PATENT DOCUMENTS 9,604,740 B2 *  3/2017  Py .......................... B65B 39/12
2012/0261027 A1  10/2012  Py
(Continued)

FOREIGN PATENT DOCUMENTS

DE   102010028499 A1   11/2011
DE   102014202123 A1   8/2015

OTHER PUBLICATIONS

International Search Report with English translation and Written Opinion for Application No. PCT/EP2018/073851 dated Oct. 22, 2018 (12 pages).

*Primary Examiner* — Craig M Schneider
*Assistant Examiner* — Jason K Niesz
(74) *Attorney, Agent, or Firm* — Michael Best & Friedrich LLP

(57) ABSTRACT

The invention relates to a filling needle (10; 10a-10g) for dispensing a pharmaceutical liquid (1) into a container (2), comprising a preferably rod-shaped filling needle body (12; 12a; 12b; 12d; 12f; 12g) in which a product feed bore (13) is formed, having at least one, preferably a plurality of product outlet bores (16; 16a to 16d) which extends from the product feed bore (13) and opens on an outer wall of the filling needle body (12; 12a; 12b; 12d; 12f; 12g) into a region which is spaced apart from a filling needle body end (25; 25b; 25c) with respect to a longitudinal axis (18) of the filling needle body (12; 12a; 12b; 12d; 12f; 12g), and having a valve element (14; 14b; 14c; 14d; 14e; 14g) which is made of an elastic material which covers the filling needle body (Continued)

(12; 12*a*; 12*b*; 12*d*; 12*f*; 12*g*) at least in the region of the at least one product outlet bore (16; 16*a* to 16*d*).

14 Claims, 4 Drawing Sheets

(51) Int. Cl.
    *A61M 5/32*     (2006.01)
    *B65B 3/00*     (2006.01)
    *A61M 5/31*     (2006.01)

(56) References Cited

U.S. PATENT DOCUMENTS

2013/0333796 A1    12/2013   Py
2017/0158365 A1     6/2017   Py

\* cited by examiner

FILLING NEEDLE FOR DISPENSING A PHARMACEUTICAL LIQUID INTO A CONTAINER, AND FILLING DEVICE

BACKGROUND

The invention relates to a filling needle for dispensing a pharmaceutical liquid into a container, and to a filling device having at least one filling needle according to the invention.

Filling needles are generally used for dispensing or dosing pharmaceutical liquids into containers such as ampoules, vials or the like. The filling needles can be arranged on a filling device so that they can be raised and lowered to dip into the head regions of pharmaceutical containers, for example. The filling needles are also connected via filling tubes to a product storage container for the pharmaceutical liquid. The practice of performing the dosing of a certain amount of pharmaceutical liquid by subjecting the pharmaceutical liquid in the product storage container to positive pressure, and arranging a valve device, for example in the form of a pinch valve, in the region of the filling needle and/or in the region of the filling tube arranged between the filling needle and the product storage tank, is known. The basic structure of such a filling device is known from the applicant's DE 10 2014 2002 123 A1. In addition, it is known from DE 10 2010 028 499 A1 by the applicant to design a filling needle with two sleeve-shaped elements of a filling needle arranged coaxially to each other, wherein gas flows in the annular space between the inner and the outer element, thereby preventing contamination of the fill material during the filling procedure. The pharmaceutical liquid is dosed into the container through the element arranged in the center.

Furthermore, it is also known from the prior art to dose the filling material via filling needles which are arranged in operative connection with a piston metering device. The dosing of the filling material thus takes place via an ejection movement of a piston; it is also known to use a backward movement of the piston at the dosing end to cause the filling material to be suctioned back into the filling needle, so that no filling material drips.

The basic problem with pharmaceutical liquids, especially if they have a relatively low viscosity, is to avoid incorrect dosing due to dripping liquid, since it is relatively difficult to hold the liquid in the region of the filling needle, and/or this may require filling needles and filling devices which are relatively complex.

SUMMARY

The filling needle according to the invention, has the advantage that, with a relatively simple structural design, it reliably avoids dripping of filling material from the filling needle after the completing of the dosing process. This is substantially achieved according to the invention in that the filling needle has a filling needle body which is arranged at least in the area of a product outlet bore on the filling needle body in operative connection with and/or overlapping an elastic valve member which, after reaching a certain positive pressure in a product feed bore or at the product outlet bore, opens the flow path for the liquid pharmaceuticals in the direction of the pharmaceutical container, and in that it closes the product outlet bore below the positive pressure, thereby preventing liquid from dripping or flowing from the product outlet bore in the direction of the container.

If the cross-section of the filling needle body is circular at least in the region of the outlet of the at least one product outlet bore, it is possible to use a (sleeve-shaped) tube section as the valve element. This then seals the area of the product outlet bore particularly securely and reliably, because the valve element lies evenly on the outer circumference of the filling needle body, and, as a result, uniform and/or homogeneous tensile stresses are generated in the material of the valve element, allowing uniform contact of the valve element in the area of the outlet of the product outlet bore on the filling needle body.

In order to enable a filling jet of the liquid which is as homogeneous as possible, and/or uniform over the cross-section of the filling needle, when a plurality of product outlet bores is used, the outlets thereof in the outer wall of the filling needle body open at equal angular intervals about the longitudinal axis of the filling needle body.

To increase the flow rate at a certain positive pressure of the liquid and for a limited cross-section of the product outlet bore, for a spatially advantageous arrangement of the product outlet bores the outlets of the product outlet bores in the outer wall of the filling needle body can open in at least two different regions with respect to the longitudinal axis of the filling needle body.

With regard to the axial length and exact position of the (tubular) valve element in relation to the end of the filling needle body facing the pharmaceutical container, there are basically two different possibilities: In a first embodiment, the valve element is sleeve-shaped, and it projects beyond the filling needle body end when viewed in the direction of the longitudinal axis. Such an embodiment ensures in particular that any liquid present in the area of the filling needle body end can collect on the inner circumference of the valve element. As an alternative to this, however, in a second embodiment, the valve element is sleeve-shaped, the filling needle body end is conical, and the valve element ends in the conical region as seen in the direction of the longitudinal axis. Such an embodiment particularly has the advantage that one of the end faces of the valve element can abut and/or nestle against the filling needle body in the region of the conical filling needle body end. A filling jet with a reduced cross-section is thus generated upon release, additionally offering the advantage that the product flows out of the filling needle in a non-turbulent or laminar manner, thereby also avoiding air pockets in the product and/or in the container which is filled.

In a further constructive embodiment of the filling needle body, a cross-sectional reduction extends radially around the longitudinal axis of the filling needle body. Such an embodiment particularly has the advantage that when liquid is suctioned back, the valve element can nestle against the filling needle body in the region of the cross-section reduction, thereby ensuring a particularly good sealing effect.

In a further development of the latter suggestion, it can in particular be provided that the cross-sectional reduction has a rounded cross-section. This has the particular advantage that the valve element can nestle or fit against the outer wall of the filling needle body without a gap.

A separate fastening element or a form-fitting connection on the filling needle body is preferably used for connecting the valve element to the filling needle body. These types of fastening also make it possible for the valve element to be exchanged in a relatively simple manner and for the valve element to be held particularly securely on the filling needle body.

A further embodiment of the invention relates to a filling device having at least one filling needle according to the invention as described to this point, wherein the filling device is characterized in that it has means for suctioning liquid back into the filling needle body. By suctioning liquid back into the filling needle body when the dosing is finished, on the one hand a further escape of liquid from the filling needle body in the direction of the pharmaceutical container is reliably avoided, and on the other hand the valve element is placed against the outlet of the product outlet bore by the negative pressure thereby generated, thereby enabling a particularly secure and reliable sealing of the product outlet bore on the filling needle body.

BRIEF DESCRIPTION OF THE DRAWINGS

Further advantages, features and details of the invention can be found in the following description of a preferred embodiment and with reference to the drawings,
wherein.

DETAILED DESCRIPTION

Figure 1:
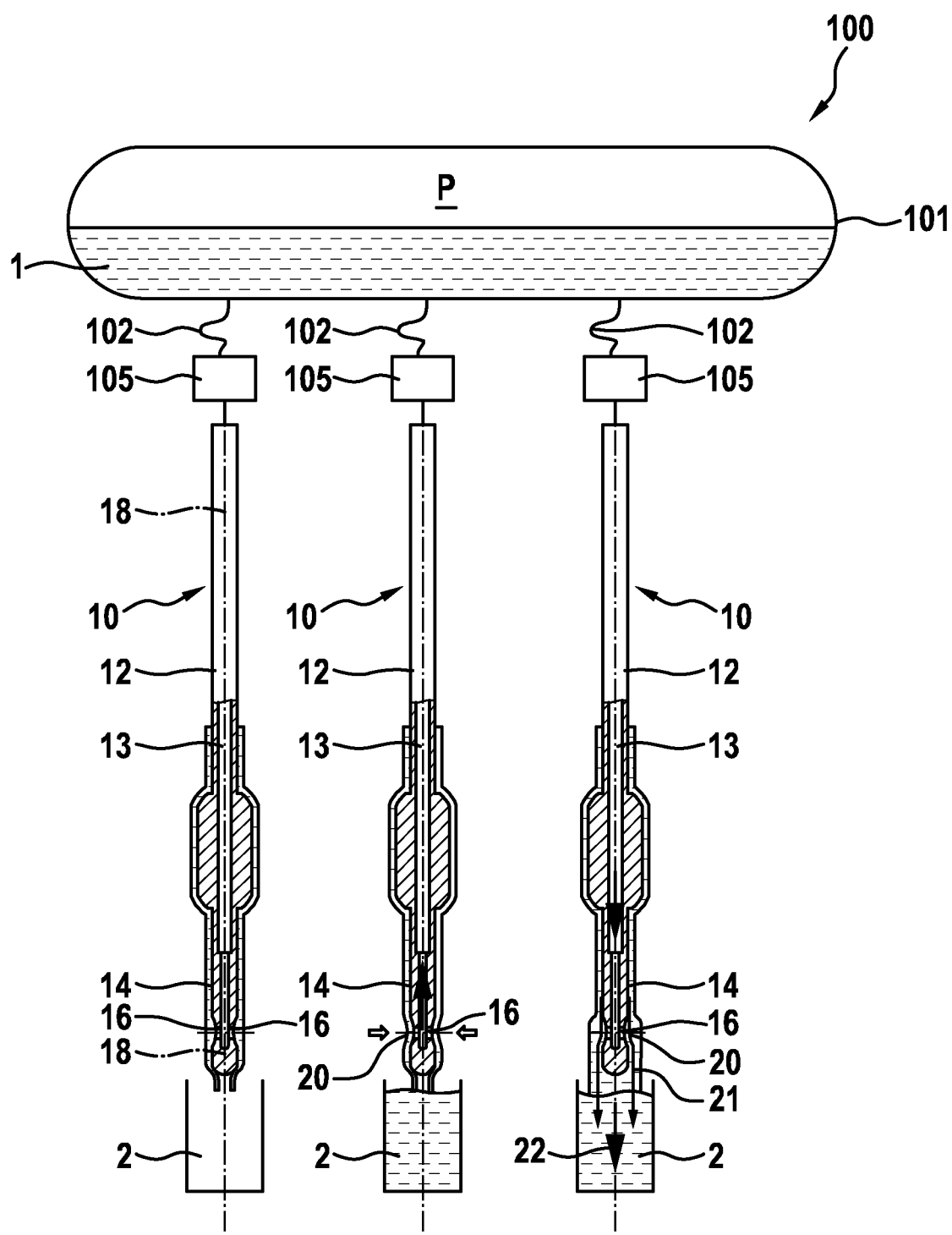
FIG. 1 shows a simplified illustration of a filling device for dosing liquid pharmaceuticals into containers, and
FIGS. 2 to 8 each show an end region of a filling needle facing a container, in different structural configurations.
The same elements, and/or elements having the same function, are provided with the same reference numbers in the figures.

FIG. 1 shows a filling device 100 for dispensing and/or dosing a pharmaceutical liquid 1 into pharmaceutical containers 2, for example ampoules, vials or the like, in a highly simplified illustration. The pharmaceutical liquid 1 is, in particular, a low-viscosity or relatively-low surface tension liquid 1, or a liquid capable of creep, in particular oil-based or alcohol-based.

The filling device 100 comprises a product storage tank 101 for the liquid 1, in which the liquid 1 is stored, for example, under a certain positive pressure P. A plurality of filling tubes 102 extend from the product storage tank 101, and are each connected to a filling needle 10 according to the invention, with, by way of example, a piston metering device 105 connecting in-between. The piston metering device 105 is designed to convey a certain amount of liquid 1 in accordance with a feed path and/or stroke of a piston in the direction of the filling needle 10, and to suction liquid 1 back out of the filling needle 10 when the piston, which is not shown in FIG. 1, moves backwards.

Each filling needle 10 substantially has a pin-shaped or cylindrical filling needle body 12, preferably made of metal, which is radially surrounded on the end area thereof facing the container 2 by a sleeve-shaped, tubular valve element 14 made of an elastic material such as an elastomer. A product feed bore 13 is formed in the filling needle body 12, for example in the form of a blind hole, from which preferably a plurality of radially outwardly projecting product outlet bores 16 extend at uniform angular intervals about the longitudinal axis 18 of the filling needle body 12, and then open on the outer surface of the filling needle body 12 in the area of overlap with the valve element 14.

In addition, it is mentioned that the filling needle body 12, as is known and customary per se from the prior art, can also be designed as a tube which is configured in the region of the end region facing the container 2 with a closure piece which is inserted into the opening of the tube and seals the same.

Furthermore, the valve element 14 can either be formed from a product-repellent material, or at least is provided with a corresponding coating on the (inner) side facing the filling needle body 12 in order to inhibit and/or prevent product from sticking between the valve element 14 and the filling needle body 12.

Product outlet bores 16 in the context of the invention are not only to be understood as bores in the narrower sense (that is, openings with a round cross-sectional area), but all product outlet openings, regardless of their cross-sectional shape or the way in which they were produced, such as, for example, by a laser beam device.

FIG. 1 shows three filling needles 10 during different dosing phases of the liquid 1, for the sake of simplicity and to clarify the function of the valve element 14. It is of course within the scope of the invention that the filling device 100 has more than three filling needles 10, which are arranged, for example, at equal intervals from each other in order to fill the containers 2 conveyed below the filling needles 10 in a clocked cycle by means of a conveying device, which is not shown. Furthermore, the filling needles 10 are actuated together and/or identically during the filling operation, such that the three dosing phases briefly explained below take place simultaneously on all filling needles 10 of the filling device 100.

The filling needle 10 shown at left in FIG. 1 is shown in an operating state of the filling device 100, in which the valve element 14 closes the product outlet bores 16 formed on the filling needle body 12 in order to prevent a discharge of liquid 1 into the container 2. In this case, at most only a relatively low positive pressure is present in the region of the product outlet bores 16, which ensures a seal between the filling needle body 12 and the valve element 14 against leakage of liquid 1 in the direction of the container 2.

In contrast, the state in which liquid 1 is suctioned back out of the filling needle 10 by means of the piston metering device 105 is shown for the center filling needle 10 in FIG. 1. In this case, the valve element 16 nestles against the filling needle body 12 in the region of a cross-sectional taper 20 which is formed radially about a longitudinal axis 18 and is arranged in the region of the at least one product outlet bore 16.

Finally, the filling needle 10 at right in FIG. 1 shows the filling operation in which, by means of the piston metering device 105 in the filling needle body 12 and/or the product outlet bore 16, the liquid 1 has a positive pressure which is high enough so that the valve element 14 is expanded radially in the region of the product outlet bore 16. The liquid 1 reaches the radial annular space between the filling needle body 12 and the inner circumference of the valve element 14 according to the arrows 21, and, at the end of the filling needle body 12, flows in the direction of the container 2, which is represented by the arrow 22.

Figure 2:
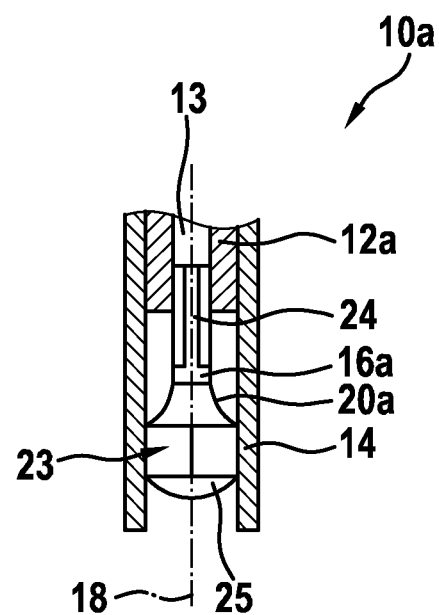

A portion of a filling needle 10a is shown in FIG. 2; the cross-sectional taper 20a is formed in a separate component 23 which functions as a sealing plug for the tubular filling needle body 12a. The product feed bore 13 in the filling needle body 12a is connected to a blind hole 24 in the component 23. The product outlet bores 16a in turn extend from the blind hole 24. Furthermore, the cross-sectional taper 20a has a cross-section which is at least partially rounded. The cross-sectional taper 20a results in a more uniform distribution of the liquid on the inner circumference of the valve element 14. Furthermore, the filling needle body end 25 is rounded or spherical, and the valve element 14, which is made of an elastic material, projects beyond the filling needle body end 25 in the axial direction along the longitudinal axis 18. In addition, the product outlet bores 16a do not have to run perpendicular to the longitudinal axis 18; rather, they can be arranged at an oblique angle, for example.

Figure 3:
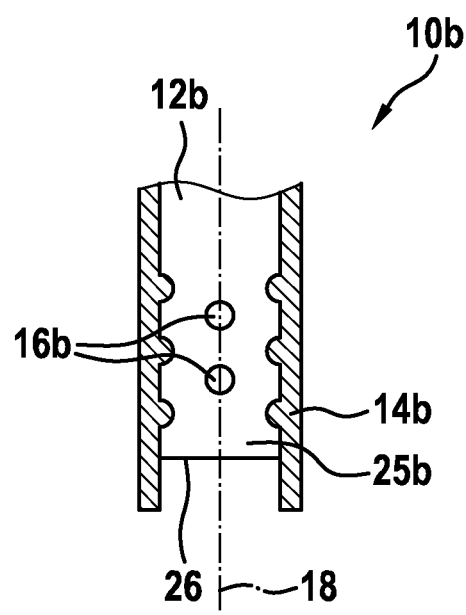

FIG. 3 shows a filling needle 10b in which a plurality of product outlet bores 16b are provided in at least two regions which are spaced apart axially with respect to the longitudinal axis 18. The product outlet bores 16b are preferably arranged at uniform angular intervals about the longitudinal axis 18 of the filling needle body 12b. For example, the filling needle body end 25b is designed with an end face 26 running perpendicular to the longitudinal axis 18. The filling needle 10b also has a particularly uniform distribution of the liquid 1 on the inner circumference of the valve element 14b.

Figure 4:
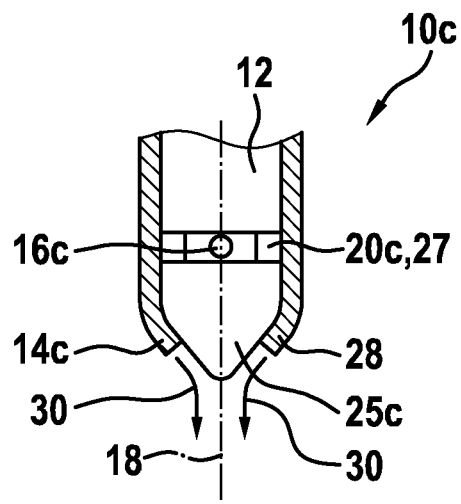

In the case of the filling needle 10c shown in FIG. 4, there is an approximately conical filling needle body end 25c. In addition, the product outlet bores 16c are formed in the region of a cross-sectional constriction 20c, which is designed as an annular groove 27 having a rectangular cross-section. The valve element 14c does not protrude beyond the filling needle body end 25c; rather, it ends shortly before it in the axial direction, such that, due to the valve element 14c which abuts the outer wall of the filling needle body 12c with an elastic tension, an end region 28 of the valve element 14c nestles against the filling needle body end 25c in the radial direction with respect to the longitudinal axis 18. When the liquid 1 is dispensed from the region of the filling needle body end 25c, the liquid 1 has improved radial cohesion and/or the filling jet has a smaller cross-section, which is indicated by the arrows 30.

Figure 5:
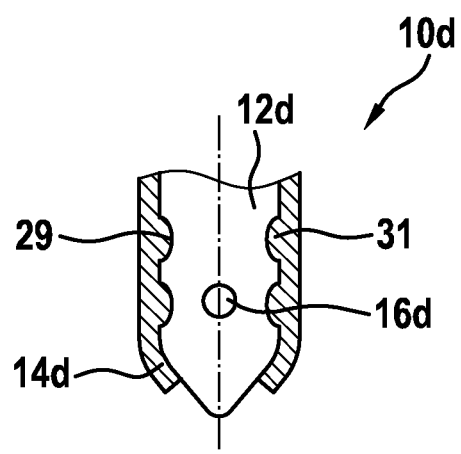

FIG. 5 shows a filling needle 10d which has an annular groove 29 directly above the product outlet bores 16d, running radially around the circumference. A radially circumferential thickening 31 of the valve element 14d projects into this annular groove 29 in order to position or fix the valve element 14d on the filling needle body 12d. The small axial distance between the attachment of the valve element 14d and the product outlet bores 16d results in a lower product retention quantity.

Figure 6:
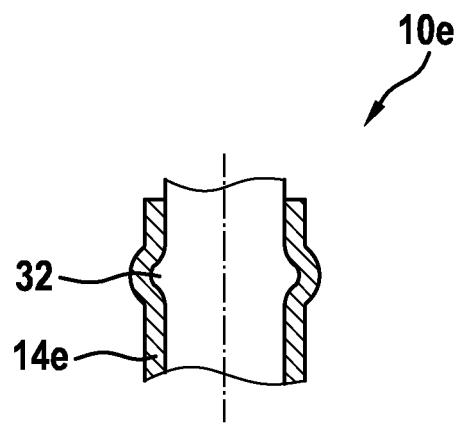

In contrast, the filling needle 10e according to FIG. 6 has a radially circumferential thickening 32, in the area of which the valve element 14e is held on the filling needle body 14e under increased circumferential tension. The thickening 32 produces a seal on both sides of the thickening 32 by means of the valve element 14e.

Figure 7:
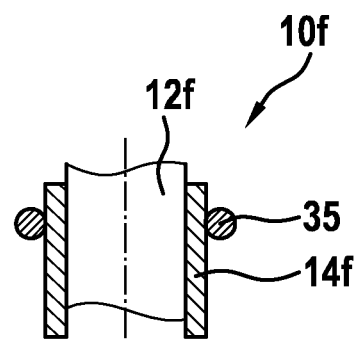

In the filling needle 10f according to FIG. 7, the valve element 14f is fixed to the outer circumference of the filling needle body 12f by a separate component 35, for example in the form of an O-ring or a clamping ring.

Figure 8:
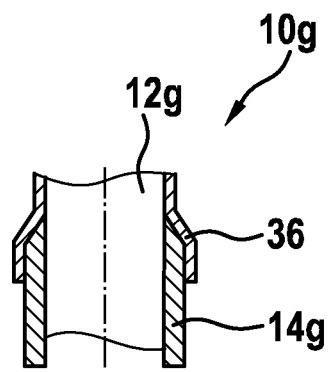

Similarly, a filling needle 10g is shown in FIG. 8 in which a clamping ring 36, which extends beyond the valve element 14g as seen in the axial direction, serves to fix or fasten the valve element 14g to the filling needle body 12g.

The filling needle 10, 10a to 10g described above can be modified or adapted in a variety of ways without deviating from the inventive concept.

The invention claimed is:

1. A filling needle (10; 10a to 10g) for dispensing a pharmaceutical liquid (1) into a container (2), the filling needle (10, 10a to 10g) comprising a filling needle body (12; 12a; 12b; 12d; 12f; 12g) in which a product feed bore (13) is formed, the filling needle (10, 10a to 10g) having at least one product outlet bore (16; 16a to 16d) communicating with the product feed bore (13) and opening to an outside of the filling needle body (12; 12a; 12b; 12d; 12f; 12g) in a region which is spaced apart from a filling needle body end (25; 25b; 25c) with respect to a longitudinal axis (18) of the filling needle body (12; 12a; 12b; 12d; 12f; 12g), and having a valve element (14; 14b; 14c; 14d; 14e; 14g) which is made of an elastic material and which covers the filling needle body (12; 12a; 12b; 12d; 12f; 12g) at least in the region of the at least one product outlet bore (16; 16a to 16d), and which opens the at least one product outlet bore (16; 16a to 16d) to dispense liquid (1) when a certain positive pressure is reached in the product outlet bore (16; 16a to 16d), and closes the at least one product outlet bore (16; 16a to 16d) when the pressure falls below said certain positive pressure.

2. The filling needle according to claim 1, characterized in that the cross-section of the filling needle body (12; 12a; 12b; 12d; 12f; 12g) is circular at least in the region of the at least one product outlet bore (16; 16a to 16d).

3. The filling needle according to claim 1, characterized in that when a plurality of product outlet bores (16; 16a to 16d) is used, their respective outlets open in the outer wall of the filling needle body (12; 12a; 12b; 12d; 12f; 12g) at uniform angular intervals about the longitudinal axis (18).

4. The filling needle according to claim 1, characterized in that when a plurality of product outlet bores (16b) is used, their respective outlets open into at least two different regions in the outer wall of the filling needle body (12b) with respect to the longitudinal axis (18).

5. The filling needle according to claim 1, characterized in that the valve element (14; 14b) is sleeve-shaped and projects beyond the filling needle body end (25; 25b) as seen in the direction of the longitudinal axis (18).

6. The filling needle according to claim 1, characterized in that the valve element (14c; 14d) is sleeve-shaped, in that the filling needle body end (25c) is conical, and in that the valve element (14c; 14d) ends in the conical region of the filling needle body end (25c) as seen in the direction of the longitudinal axis (18).

7. The filling needle according to claim 1, characterized in that the at least one outlet of a product outlet bore (16c) is formed in a region of a cross-sectional taper (20c) of the filling needle body (12) which runs radially about the longitudinal axis (18).

8. The filling needle according to claim 7, characterized in that the cross-sectional taper (20c) is in the form of an annular groove (27).

9. The filling needle according to claim 1, characterized in that the at least one product outlet bore (16a) is formed in a component (23) which is separate from the filling needle body (12) and serves as a closure for the filling needle body (12), in that the outlet of the at least one product outlet bore (16a) is formed in a region of a cross-sectional taper (20a) running radially around the component (23) about the longitudinal axis (18), and in that the cross-sectional taper (20a) has a rounded cross-section.

10. The filling needle according to claim 1, characterized in that the valve element (14; 14b; 14c; 14d; 14e; 14g) is fastened to the filling needle body (12; 12a; 12b; 12d; 12f; 12g) by a separate fastening element (36; 36) or a positive connection.

11. The filling needle according to claim 1, characterized in that the valve element (14; 14b; 14c; 14d; 14e; 14g) is made of a product-repellent material or is provided with a product-repellent coating on an inner side facing the filling needle body (12; 12a; 12b; 12d; 12f; 12g).

12. A filling device (100) having at least one filling needle (10; 10a to 10g) according to claim 1, and having means for sucking back liquid (1) in the filling needle body (12; 12a; 12b; 12d; 12f; 12g).

13. The filling needle according to claim 1, characterized in that the at least one product outlet bore (16; 16a to 16d) includes a plurality of product outlet bores (16; 16a to 16d).

14. The filling needle according to claim 1, characterized in that the filling needle body (12; 12: 12*b*; 12*d*; 12*f*; 12*g*) is rod-shaped.

* * * * *